US008257737B2

(12) United States Patent
Intini et al.

(10) Patent No.: US 8,257,737 B2
(45) Date of Patent: Sep. 4, 2012

(54) TISSUE IMPLANTS AND METHODS FOR MAKING AND USING SAME (76) Inventors: Giuseppe Intini, Buffalo, NY (US);
Sebastiano Andreana, Buffalo, NY (US); Rosemary Dziak, Amherst, NY (US); Libuse Anna Bobek, Williamsville, NY (US)

( * ) Notice: Subject to any disclaimer, the term of this patent is extended or adjusted under 35 U.S.C. 154(b) by 234 days.

(21) Appl. No.: 10/216,552

(22) Filed: Aug. 9, 2002

(65) Prior Publication Data
US 2003/0143211 A1 Jul. 31, 2003

Related U.S. Application Data (60) Provisional application No. 60/311,216, filed on Aug. 9, 2001.

(51) Int. Cl.
*A61K 9/14* (2006.01)
*A01N 43/04* (2006.01)
*A01K 67/00* (2006.01)

(52) U.S. Cl. ..................................... 424/484
(58) Field of Classification Search ................. 424/426; 514/44; 435/320.1, 455
See application file for complete search history.

(56) References Cited

U.S. PATENT DOCUMENTS

| | | | |
|---|---|---|---|
| 4,868,116 A | 9/1989 | Morgan et al. | |
| 4,963,489 A | 10/1990 | Naughton et al. | |
| 4,980,286 A | 12/1990 | Morgan et al. | |
| 5,034,352 A | 7/1991 | Vit et al. | |
| 5,147,403 A | 9/1992 | Gitelis | |
| 5,399,346 A | 3/1995 | Anderson et al. | |
| 5,425,769 A | 6/1995 | Snyders, Jr. | |
| 5,603,943 A | 2/1997 | Yanagawa | |
| 5,614,206 A | 3/1997 | Randolph et al. | |
| 5,807,567 A | 9/1998 | Randolph et al. | |
| 5,849,331 A * | 12/1998 | Ducheyne et al. ............ 424/484 |
| 5,942,496 A | 8/1999 | Bonadio et al. | |
| 5,962,427 A | 10/1999 | Goldstein et al. | |
| 6,022,887 A | 2/2000 | Gasper et al. | |
| 6,030,636 A * | 2/2000 | Randolph et al. ............. 424/426 |
| 6,037,116 A | 3/2000 | Wiggins et al. | |
| 6,080,779 A | 6/2000 | Gasper et al. | |
| 6,150,328 A | 11/2000 | Wang et al. | |
| 6,179,872 B1 | 1/2001 | Bell et al. | |
| 6,361,933 B1 | 3/2002 | Wiggins et al. | |
| 2003/0003125 A1* | 1/2003 | Nathan et al. ................. 424/408 |
| 2003/0103960 A1* | 6/2003 | Philippart et al. ......... 424/94.64 |
| 2009/0098204 A1 | 4/2009 | Intini et al. | |

FOREIGN PATENT DOCUMENTS

| | | |
|---|---|---|
| WO | WO 87/00201 | 1/1987 |
| WO | WO 89/05345 | 6/1989 |
| WO | WO 89/07136 | 8/1989 |
| WO | WO 90/11092 | 10/1990 |
| WO | WO 95/28950 | * 11/1995 |

OTHER PUBLICATIONS

Abstract 2290, Aichelmann-Reidy et al., "Evaluation of Calcium Sulfate Barrier for the Treatment of Intrabony Defects" (2002).
Abstract 3451, Sen et al., "Platelet-Derived Growth Factor Adsorption on Calcium Sulfate: Effects on Osteoblast Activity" (2002).
Kim et al., "Use of Particulate Dentin-Plaster of Paris Combination with/without Platelet-Rich Plasma in the Treatment of Bone Defects Around Implants," *Int. J. Oral Maxillofac Implants*, vol. 17(1):86-94 (2002).
Payne et al., "Migration of Human Gingival Fibroblasts Over Guided Tissue Regeneration Barrier Materials," *J. Periodontol.* 67(3):236-244 (1996) (abstract only).
Lifecore Biomedical, Inc., "Regeneration Products: CAPSET® Calcium Sulfate Bone Graft Barrier" (copyright 2001) at http://www.lifecore.com/products/capset.asp (visited Aug. 8, 2002).
Wright Medical Technology, Inc., "OSTEOSET® Bone Graft Substitute" (copyright 2001) at http://www.wmtcom/Physicians/ProductDetail:asp?CatID=1&id=-719559978 (visited Aug. 8, 2002).
Wright Medical Technology, Inc., "OSTEOSET® Bone Graft Substitute: Surgical Grade Calcium Sulfate" (copyright 1999).
Osteogenic Core Technologies, Inc., "How to Concentrate Platelet and Make it Gel" (copyright 1999-2001) at http://www.octusa.com/support/Centrifuge.html (visited Aug. 9, 2002).
Osteogenic Core Technologies, Inc., "Platelet Concentrator (PLACON)" (copyright 1999-2001) at http://www.octusa.com/product/Centrifuge.html (visited Aug. 8, 2002).
Biocytex, "Platelet GelSep®" (version Feb. 2002).
J.T. Baker, "(MSDS) Material Safety Data Sheet: Calcium Sulfate, ½-Hydrate, Powder" at file:///Fi/Doug/MSDS/Calcium Sulfate, 1-2-Hydrate, Powder.htm (visited Jun. 19, 2000).
Biospace CCIS, "BioSpace News: Lifecore Biomedical" (May 20, 2002) at http://www.biospace.com/ccis/news_company.cfm?CompanyID=2317 (visited Aug. 8, 2002).
Graham & Van Der Eb, A New Technique for the Assay of Infectivity of Human Adenovirus 5 DNA, *Virol.* 52:456-67 (1973).
INTIN1, Tissue-engineering of an Efficient Bone Graft Material: Modifications of Calcium Sulfate (Aug. 11, 2000) (M.S. thesis, S.U.N.Y. Buffalo).

(Continued)

*Primary Examiner* — Quang Nguyen
(74) *Attorney, Agent, or Firm* — Hodgson Russ LLP (57) ABSTRACT

The invention provides biocompatible, biodegradable calcium sulfate matrices containing calcium sulfate activated platelets for use in tissue formation. The matrices are particularly useful in stimulating hard tissue, for example, bone formation. The matrices may also further include a growth factor and/or a transfectable gene, the inclusion of which may be useful in stimulating the growth of tissue of interest.

32 Claims, 4 Drawing Sheets

OTHER PUBLICATIONS

Alexander et al., "Efficacy of Calcium Sulfate Plus Decompression Bone in Lumbar and Lumbosacral Spinal Fusion: Preliminary Results in 40 Patients," *Canad. J. Surg.* 44(4):262-6 (2001).

Andreana, "A Combined Approach for Treatment of Developmental Groove Associated Periodontal Defect," *J. Periodontal.* 69:601-7 (1998).

Andreana, "Management of a Trifurcation with Calcium Sulfate and Nonabsorbable Membrane: 18-Month Follow-up," *Periodont. Insights* 5:5-7(1998).

Anson et al., "Towards Gene Therapy for Hemophilia B," *Mol. Biol. Med.* 4:11-20 (1987).

Anson, "Calcium Sulfate: A 4-Year Observation of Its Use as a Resorbable Barrier in Guided Tissue Regeneration of Periodontal Defects," *Compend. Contin. Educ. Dent.* 17(8):895-9 (1996).

Blaese et al., "T Lymphocyte-directed Gene Therapy for ADA SCID: Initial Trial Results After 4 Years," *Science* 270:475-80(1995).

Bonadio et al., "Gene Therapy for Tissue Repair and Regeneration," *Adv. Drug Deliv. Rev.* 33(1-2):53-69 (1998).

Bonadio et al., "Localized, Direct Plasmid Gene Delivery in Vivo: Prolonged Therapy Results in Reproducible Tissue Regeneration," *Nat. Med.* 5(7):753-59 (1999).

Bonadio, "Tissue Engineering Via Local Gene Delivery," *J. Mol. Med.* 78(6):303-11 (2000).

Brass, "The Molecular Basis for Platelet Activation," in Hematology 1753-70 (Ronald Hoffman et al. eds., $3^{rd}$ ed. 2000).

"Calcium Sulfate Processing," *NOSB TAP Materials Database* 1-15 (compiled by OMRI, 2001).

Calhoun et al., "Effects of Plaster of Paris Implants on Osteogenesis in the Mandible of Dogs," *J. Dent. Res.* 42:1244 (1963).

Gader et al., "Direct Activation of Platelets by Heat Is the Possible Trigger of the Coagulopathy of Heat Stroke," *Brit. J. Haematol.* 74:86-92 (1990).

Kurabayashi et al., "Effects of Hypertherrnal Stress on the Ultrastructure of Platelets with Reference to the Localization of Platelet Peroxidase and Fibrinogen in Vivo," *Amer. J. Hematol.* 56:244-7 (1997).

Ledley et al., "Retroviral Gene Transfer into Primary Hepatocytes: Implications for Genetic Therapy of Liver-specific Functions," *Proc. Nat'l Acad Sci. U.S.A.* 84:5335-9 (1987).

Ledley, "Somatic Gene Therapy for Human Disease: Background and Prospects. Part I," *J. Pediatr.* 110(1):1-9 (1987).

Lim et al., "Long-term Expression of Human Adenosine Deaminase in Mice Transplanted with Retrovirus-infected Hematopoietic Stem Cells," *Proc. Nat'l Acad. Sci. U.S.A.* 86:8892-6 (1989).

Malmgren, "ATP-secretion Occurs as an Initial Response in Collagen Induced Platelet Activation," *Thromb. Res.* 43:445-53 (1986).

Marx et al., "Platelet-rich Plasma: Growth Factor Enhancement for Bone Grafts," *Oral Surg. Oral Med. Oral. Pathol.* 85(6):638-46 (1998).

Morgan et al., "Expression of an Exogenous Growth Hormone Gene by Transplantable Human Epidermal Cells," *Science* 237:1476-9 (1987).

Nicolau et al., "In Vivo Expression of Rat Insulin After Intravenous Administration of the Liposome-entrapped Gene for Rat Insulin I," *Proc. Nat'! Acad. Sci. U.S.A.* 80:1068-72 (1983).

Palmer et al., "Efficient Retrovirus-mediated Transfer and Expression of a Human Adenosine Deaminase Gene in Diploid Skin Fibroblasts from an Adenosine Deaminase-deficient Human," *Proc. Nat'l Acad. Sci. U.S.A.* 84:1055-9 (1987).

Pecora et al., "Bone Regeneration with a Calcium Sulfate Barrier," *Oral Surg. Oral Med. Oral Pathol. Oral Radiol. Endod.* 84(4):424-9 (1997).

Peltier, "The Use of Plaster of Paris to Fill Large Defects in Bone," *Am. J. Surg.* 97:311-5 (1959).

Plow & Ginsberg, "The Molecular Basis for Platelet Function," in Hematology 1741-52 (Ronald Hoffman et al. eds., $3^{rd}$ ed. 2000).

Rosenberg et al., "Grafting Genetically Modified Cells to the Damaged Brain: Restorative Effects of NGF Expression," *Science* 242:1575-8 (1988).

Sato et al., "Osteogenic Response of Rabbit Tibia to Hydroxyapatite Particle-Plaster of Paris Mixture," *Biomat.* 19:1895-1900 (1998).

Shaffer & App, "The Use of Plaster of Paris in Treating Infrabony Periodontal Defects in Humans," *J. Periodont.* 42(11):685-90 (1971).

Sidqui et al., "Osteoblast Adherence and Resorption Activity of Isolated Osteoclasts on Calcium Sulphate Hemihydrate," *Biomal.* 16:1327-32 (1995).

Sottosanti, "Aesthetic Extractions with Calcium Sulfate and the Principles of Guided Tissue Regeneration," *Pract. Periodont. Aesthetic. Dent.* 5(5):61-9 (1993).

Sottosanti, "Calcium Sulfate Is a Safe, Resorbable Barrier Adjunct to Implant Surgical Procedures," *Dent. Implantol. Update* 4(9):69-73 (1993).

Sottosanti, "Calcium Sulfate: A Biodegradable and Biocompatible Barrier for Guided Tissue Regeneration," *Compend. Cont. Educ. Dent.* 13(3):226-8, 230, 232-4 (1992).

Wichelhaus et al., "Elution Characteristics of Vancomycin, Teicoplanin, Gentamicin and Clindamycin from Calcium Sulphate Beads," *J. Antimicrob. Chemother.* 48:117-9 (2001).

Wilson et al., "Temporary Amelioration of Hyperlipidemia in Low Density Lipoprotein Receptor-deficient Rabbits Transplanted with Genetically Modified Hepatocytes," *Proc. Nat'l Acad. Sci. U.S.A.* 87:8437-41 (1990).

Wolff et al., "Expression of Retrovirally Transduced Genes in Primary Cultures of Adult Rat Hepatocytes," *Proc. Nat'l Acad. Sci. U.S.A.* 84:3344-8 (1987).

Aframian et al., "The Growth and Morphological Behavior of Salivary Epithelial Cells on Matrix Protein-coated Biodegradable Substrata," Tissue Engin'g 6(3):209-16 (2000).

Cornelini et al., "Trattamento Regenerativo di Lesioni Parodontali Complesse con Solfato di Calcio. Caso Clinico [Regenerative Treatment of Complex Periodontal Lesions with Calcium Sulfate. Case Report]," Quintessence Int'l 16 (1/2):19-23 (2000).

Kocher et al., "Neovascularization of Ischemic Myocardium by Human Bone-marrow-derived Angioblasts Prevents Cardiomyocyte Apoptosis, Reduces Remodeling and Improves Cardiac Function," Nat. Med. 7(4):430-36 (2001).

Mahoney & Saltzman, "Transplantation of Brain Cells Assembled Around a Programmable Synthetic Microenvironment," Nat. Biotech. 19:934-39 (2001).

Orlic et al., "Bone Marrow Cells Regenerate Infarcted Myocardium," Nature 410:701-05 (2001).

Ralph W. Phillips, Science of Dental Materials (John Dyson ed., 9th ed. 1991) (Table of Contents).

Richardson et al., "Polymeric System for Dual Growth Factor Delivery," Nat. Biotech. 19:1029-34 (2001).

Ross et al., "The Biology of Platelet-derived Growth Factor," Cell 46:155-69 (1986).

Shanaman et al., "Localized Ridge Augmentation Using GBR and Platelet-rich Plasma: Case Reports," Int'l J. Periodont. Restor. Dentistry 21(4):345-55 (2001).

Shea et al., "DNA Delivery from Polymer Matrices for Tissue Engineering," Nat. Biotech. 17:551-54 (1999).

Shea et al., "Engineered Bone Development from a Pre-osteoblast Cell Line on Three-dimensional Scaffolds," Tissue Engin'g 6(6):605-17 (2000).

* cited by examiner

TISSUE IMPLANTS AND METHODS FOR MAKING AND USING SAME

RELATED APPLICATIONS

This application claims the benefit of U.S. patent application Ser. No. 60/311,216, filed on Aug. 9, 2001, the disclosure of which is incorporated by reference herein.

FIELD OF THE INVENTION

This invention relates generally to tissue repair, and more particularly to a bioactive matrix, methods of making such a matrix, and methods of using such a matrix for promoting hard tissue formation.

BACKGROUND OF THE INVENTION

The formation of bone is a dynamic process that starts during embryogenesis and continues, though remodeling, during adult life. Occasionally, bone can also be regenerated when bone repair is needed. A complex series of events, involving cellular growth and differentiation together with extracellular matrix formation, are required for bone formation. A similar sequence of events takes place during bone repair.

The process of bone repair and regeneration resembles the process of wound healing in other tissues. In general, in response to injury, mesenchymal cells from the surrounding tissue migrate into the wound site and differentiate into cartilage or bone cells. A typical sequence of events includes: hemorrhage; clot formation; dissolution of the clot with concurrent removal of damaged tissues; ingrowth of granulation tissue; formation of cartilage; capillary ingrowth and cartilage turnover; rapid bone formation (callus tissue); and, finally, remodeling of the callus into cortical and trabecular bone. Bone repair, therefore, is a complex process that involves many cell types and regulatory molecules. The diverse cell populations involved in fracture repair include stem cells, macrophages, fibroblasts, vascular cells, osteoblasts, chondroblasts, and osteoclasts.

Many growth factors are also involved in the regeneration process. These include, for example, members of the bone morphogenic protein (BMP) family, fibroblast growth factor (FGF), platelet-derived growth factor (PDGF), and members of the insulin growth factor (IGF) family. PDGF, for example, has been shown to stimulate bone cell replication and DNA synthesis both in intact calvaria and isolated rat osteoblasts. Other growth factors or hormones that have been reported to have the capacity to stimulate new bone formation include acidic fibroblast growth factor, estrogen, macrophage colony stimulating factor, and calcium regulatory agents such as parathyroid hormone (PTH).

Other regulatory factors involved in bone repair are known to include systemic hormones, cytokines, growth factors, and other molecules that regulate growth and differentiation. Various osteoinductive agents have been purified and shown to be polypeptide growth-factor-like molecules. A rich source of osteogenic growth factors is found in platelet-rich plasma. The platelets possess granules that contain such growth factors as PDGF, TGF-$\beta$ and others, which aid in accelerating angiogenesis and osteogenesis.

The techniques of bone reconstruction, such as is used to reconstruct defects occurring as a result of trauma, cancer surgery or errors in development, would be improved by new methods to promote bone repair. Reconstructive methods currently employed, such as using autologous bone grafts, or bone grafts with attached soft tissue and blood vessels, are associated with significant drawbacks of both cost and difficulty. For example, harvesting a useful amount of autologous bone is not easily achieved, and even autologous grafts often become infected or suffer from resorption.

Prior methods of inducing bone growth have used synthetic implants, or matrices, to support bone growth using materials, such as collagen. In designing a bioactive matrix, particular consideration must be given to the following features: biocompatability, scaffolding (the ability of a matrix to allow migration and proliferation of tissue specific cells), filling (the capacity of filling and therefore preserving the original shape of the regeneration site), barrier effect (the ability of excluding non-related cells from repopulation of the regeneration site), and carrier function (the ability of the engineered graft to carry and deliver bioactive factors). However, one of the most important limitations in designing a bioactive matrix remains the inability to determine which of the growth factors and cell adhesion molecules eventually favor and control histogenesis.

Several groups have investigated the possibility of using bone stimulating proteins and polypeptides, to influence bone repair in vivo. However, there are many drawbacks associated with these type of treatment protocols, including the time and expense in purifying recombinant proteins. Also, once administered to an animal, polypeptides may be more unstable than is generally desired for a therapeutic agent, and they may be susceptible to proteolytic attack. Furthermore, the administration of recombinant proteins can initiate various inhibitory or otherwise harmful immune responses. Further limitations often are related to the inability of the carrier to deliver significant levels of the an active agent to the desired growth locus. For example, many materials have been tested for sustained release of PDGF. Poly-L-lactide (PLLA), although it is commonly used, appears to be resorbed too quickly. Modifications of PLLA have been proposed as polylactic-co-glycolic acid (PLGA) with an improved and prolonged resorption rate. However, in both cases, cell attachment can be limited. Also, these polyhydroxy acids can generate acidic degradation bioproducts at the implanted sites with undesirable tissue reaction. Recently, other modifications have been proposed such as the combination of PLLA with chitosan (a synthetic compound structurally similar to glycosaminoglycan in the extracellular matrix) to limit the tissue reaction due to the acidic compound and improve cell attachment. Also, collagen disks or methylcellulose gel have been used to deliver PDGF with limited results due to their rapid resorption rate. The anionic characteristic of hydroxyapatite crystals has been recently used to deliver cationic bioactive molecules such as PDGF. The bone tissue regenerated in this case is qualitatively altered by the presence of synthetic hydroxyapaptite, a non-resorbable compound. In each of these cases, some of the required properties of a biomatrix are essentially missing. In some instances scaffolding is given up to favor releasing, or in other cases is the tissue-filing that is given up in favor of scaffolding.

In addition to growth factor therapy, prior methods of inducing bone growth have contemplated the use of gene therapy. However, currently there are some limitations in delivering plasmid DNA in tissues other than liver and muscle. Initial efforts toward somatic gene therapy have relied on indirect means of introducing genes into tissues, called ex vivo gene therapy, e.g., target cells are removed from the body, transfected or infected with vectors carrying recombinant genes, and re-implanted into the body ("autologous cell transfer"). A variety of transfection techniques currently are available that can be used to transfer DNA into cells in vitro; including calcium phosphate-DNA precipitation, DEAE-Dextran transfection, electroporation, liposome mediated DNA transfer or transduction with recombinant viral vectors. Such ex vivo treatment protocols have been proposed to transfer DNA into a variety of different cell types including epithelial cells (U.S. Pat. No. 4,868,116; Morgan and Mulligan WO87/00201; Morgan et al., 1987, Science 237:1476-1479; Morgan and Mulligan, U.S. Pat. No. 4,980,286), endothelial cells (WO89/05345), hepatocytes (WO89/07136; Wolff et al., 1987, Proc. Natl. Acad. Sci. USA 84:3344-3348; Ledley et al., 1987 Proc. Natl. Acad. Sci. 84:5335-5339; Wilson and Mulligan, WO89/07136; Wilson et al., 1990, Proc. Natl. Acad. Sci. 87:8437-8441), fibroblasts (Palmer et al., 1987, Proc. Natl. Acad. Sci. USA 84:1055-1059; Anson et al., 1987, Mol. Biol. Med. 4:11-20; Rosenberg et al., 1988, Science 242:1575-1578; Naughton & Naughton, U.S. Pat. No. 4,963,489), lymphocytes (Anderson et al., U.S. Pat. No. 5,399,346; Blaese, R. M. et al., 1995, Science 270: 475-480), and hematopoietic stem cells (Lim, B. et al. 1989, Proc. Natl. Acad. Sci. USA 86:8892-8896; and Anderson et al., U.S. Pat. No. 5,399,346).

To improve transfection efficiency in other tissues, several studies propose the coating of plasmid DNA with different combinations of lipids and polymers. For example, coating a DNA molecule with positively charged lipids favors uptake of DNA by the cells. Direct in vivo gene transfer has been attempted with formulations of DNA trapped in liposomes (Ledley et al., 1987, J. Pediatrics 110:1); or in proteoliposomes that contain viral envelope receptor proteins (Nicolau et al., 1983, Proc. Natl. Acad. Sci. U.S.A. 80:1068); and DNA coupled to a polylysine-glycoprotein carrier complex. In addition, "gene guns" have been used for gene delivery into cells (Australian Patent No. 9068389). It has even been speculated that naked DNA, or DNA associated with liposomes, can be formulated in liquid carrier solutions for injection into interstitial spaces for transfer of DNA into cells (Felgner, WO90/11092).

Perhaps one of the greatest problems associated with currently devised gene therapies, whether ex vivo or in vivo, is the inability to transfer DNA efficiently into a targeted cell population and to achieve high level expression of the gene product in vivo. Viral vectors are regarded as the most efficient system, and recombinant replication-defective viral vectors have been used to transduce (i.e., infect) cells both ex vivo and in vivo. Such vectors have included retroviral, adenovirus and adeno-associated and herpes viral vectors. While highly efficient at gene transfer, the major disadvantages associated with the use of viral vectors include the inability of many viral vectors to infect non-dividing cells; problems associated with insertional mutagenesis; inflammatory reactions to the virus and potential helper virus production, and/or production and transmission of harmful virus to other human patients.

In addition to the low efficiency of most cell types to take up and express foreign DNA, many targeted cell populations are found in such low numbers in the body that the efficiency of presentation of DNA to the specific targeted cell types is even further diminished. At present, there is a need for improved methods for increasing the efficiency with which DNA is targeted to the targeted cell population.

Defects in the process of bone repair and regeneration are linked to the development of several human diseases and disorders, for example, osteoporosis and osteogenesis imperfecta. Failure of the bone repair mechanism is, of course, also associated with significant complications in clinical orthopaedic practice, for example, fibrous non-union following bone fracture, implant interface failures and large allograft failures. There, therefore, still exists a need for other matrices, and more efficient methods for making such matrices and methods of using such matrices for inducing bone growth, as well as for using such matrices in conjunction with gene therapy.

SUMMARY OF THE INVENTION

The invention provides a family of biocompatible, biodegradable matrices that can be used to promote tissue growth in a mammal. The matrices are particularly useful for stimulating hard tissue formation, for example, bone or cartilage formation, and thus can be used to repair defects in hard tissue. Under certain circumstances, it may be helpful to include platelets in the matrix, which when activated release growth factors, for example, PDGF and TGF-β, that enhance new tissue formation. Heretofore, the platelets typically have been activated by exposure to purified thrombin, for example, purified bovine thrombin. However, activation of the platelets with bovine thrombin may be undesirable because (i) the bovine thrombin may not be fully characterized and may vary from batch to batch, and (ii) this approach has the inherent risk of transmitting unwanted agents, for example, prions, from the source of the thrombin to the intended recipient of the matrix.

The invention is based, in part, upon the discovery that it is possible to activate platelets by exposing the platelets, for example, in platelet-rich plasma, to a process in which a partially or completely dehydrated exothermic salt, for example, exothermic calcium sulfate, becomes rehydrated in aqueous solution. By using this approach, it is not necessary to preactivate the platelets by exposure to thrombin. The resulting matrices contain both calcium sulfate crystals, which can be useful in supporting bone growth, and activated platelets that induce both growth. The resulting matrices, therefore, do not have the inherent problems associated with activating platelets with thrombin.

As used herein, the term "platelet-rich plasma" is understood to mean any plasma preparation that has a higher density, more preferably twice the density, and most preferably four times the density, of platelets than the blood sample from which the plasma was derived. As used herein, the term "exothermic salt" is understood to mean any salt, which when combined with an aqueous solution, increases the temperature of the solution and produces a crystalline lattice capable of supporting tissue formation. As used herein, the term "exothermic calcium sulfate" is understood to mean any calcium sulfate salt, which when combined with an aqueous solution, increases the temperature of the aqueous solution. The exothermic calcium sulfate is partially or completely dehydrated and, therefore, comprises less than two molecules of water, and more preferably less than one molecule of water per calcium ion.

In one aspect, the invention provides a method of activating platelets. The method comprises providing a platelet containing fluid sample, for example, platelet-rich plasma, at a first temperature. Then, an exothermic salt, for example, exothermic calcium sulfate, is added to the sample in an amount sufficient to increase the temperature of the sample to a threshold point. Once the solution reaches a temperature at or above the threshold point, a portion of the platelets in the sample become activated. The resulting matrix contains calcium sulfate activated platelets. The matrix can be substantially free of thrombin activity, and substantially free of thrombin activated platelets.

The term "calcium sulfate activated platelets" is understood to mean a sample or preparation of platelets in which the platelets have been activated, for example, stimulated to produce platelet-derived growth factor, by exposure of the platelets to exothermic calcium sulfate. As used herein, a platelet containing sample or preparation is understood to be "substantially free of thrombin activity," if the preparation or sample does not contain enough thrombin activity to induce a detectable increase in concentration of a soluble fibrin monomer complex in a fibrinogen containing solution when assayed via a latex agglutination assay.

In one embodiment, the sample is provided at an ambient temperature, for example, room temperature, more specifically, at about 20° C. However, the addition of the salt preferably causes the sample to increase to a temperature in the range from about 30° C. to about 50° C., and more preferably in the range from about 40° C. to about 45° C. The platelets then become activated by exposure to the elevated temperature and release certain growth factors, for example, PDGF and TGFβ.

In another aspect, the invention provides a method of promoting bone formation at a preselected locus in a mammal. The method comprises the step of providing to the locus a bioactive matrix comprising calcium sulfate and calcium sulfate activated platelets, wherein the bioactive matrix promotes bone formation at the locus. The matrix preferably is substantially free of thrombin activity and/or is substantially free of thrombin activated platelets.

In one embodiment, the method can be used to promote the formation of bone at the site of a bone defect, for example, a cavity or fracture. It is contemplated that the devices of the invention may be particularly helpful in treating non-union bone fractures.

In another embodiment, the matrix further comprises an additive such as a growth factor, an antibiotic, or another pharmaceutically active agent, or an agent for gene therapy. In one preferred embodiment, the matrix further comprises a growth factor. The matrix may contain a growth factor selected form the group consisting of BMP, FGF, PDGF, and IGF. In a preferred embodiment, however, the matrix further comprises one or more of PDGF and VEGF.

In another embodiment, the bioactive matrix further comprises a nucleic acid, for example, a vector, having a nucleotide sequence encoding a preselected gene expressible at the locus. The nucleic acid preferably is capable of being transfected into and expressed by cells at the preselected locus. Accordingly, the matrices of the invention can be used to deliver a nucleic acid encoding a sense or anti-sense nucleotide sequence to facilitate gene therapy at a preselected locus in the mammal.

It is contemplated, however, that the matrices of the invention may comprise one or more of a nucleic acid to facilitate gene therapy, a medicament, for example, a bioactive agent such as, an antibiotic, and a growth factor. It is contemplated that the choice of such additives will depend upon the intended use of the matrix.

In another embodiment, the matrix preferably is a crystalline lattice dimensioned to permit the infiltration, proliferation and differentiation of cells, for example, bone progenitor cells, for example, osteoblasts, at the preselected locus. The resulting matrix is pliable and can be manipulated to produce any shape of interest at the preselected locus. For example, the matrix may be inserted into a bone cavity or fracture and then shaped to mimic and/or interfit with the original bone structure.

In an another aspect, the invention provides a bioactive matrix comprising mixture of calcium sulfate and calcium sulfate activated platelets. The matrix is substantially free of thrombin activity and/or is substantially free of thrombin activated platelets. The tissue forming activity of the matrix may be enhanced by the incorporation of a growth factor, for example, PDGF or a BMP, into the matrix. In addition, or in the alternative, the matrix may further comprise a nucleic acid encoding, for example, a preselected gene expressible at the locus.

In another aspect, the invention provides a multifunctional bioactive matrix. The matrix comprises a first domain defining an other surface and comprising crystalline calcium sulfate and platelet-rich plasma. The first domain optionally further comprises a first growth factor. Disposed upon, and preferably about the outer surface of, the first domain, is a second domain comprising crystalline calcium sulfate and platelet-rich plasma. The second domain optionally further comprises a second, different growth factor. However, at least one but more preferably both of the domains further comprise a growth factor.

In one embodiment, the platelet-rich plasma of the first domain comprises calcium sulfate activated platelets and/or the platelet-rich plasma of the second domain comprises calcium sulfate activated platelets. One, but preferably both, of the domains are substantially free of thrombin activity and/or are substantially free of thrombin activated platelets. Furthermore, the first domain and/or the second domain is a crystalline lattice dimensioned to permit the infiltration, proliferation and differentiation of progenitor cells, for example, bone progenitor cells, for example, osteoblasts. In one embodiment, the first domain optionally comprises a growth factor, for example, VEGF, which stimulates the formation of blood vessels. In another embodiment, the second or outer domain optionally comprises a growth factor, for example, PDGF and TGF-β, or any other growth factor that can stimulate or promote migration of cells, for example, bone progenitor cells, into the matrix. However, the choice of growth factors for incorporation into each domain or layer will depend upon the actual tissue to be created at the site of interest. This type of device permits stratified bone regeneration by attracting the appropriate bone progenitor cells. Once the cells have migrated to their preferred location, they may then be differentiated into the appropriate cell type.

DETAILED DESCRIPTION OF THE INVENTION

The invention provides a family of bioactive matrices for promoting tissue formation, more preferably, hard tissue formation, in a mammal. All of the bioactive matrices comprise a crystalline calcium sulfate matrix, and optionally comprise one or more of a variety of additives. In one embodiment, the crystalline matrices contain as the additive, activated platelets, preferably calcium sulfate activated platelets, in the form of platelet-rich plasma. In another embodiment, the crystalline matrices contain a bioactive agent, for example, an antibiotic, a growth factor or another pharmaceutically active agent, which induces or causes a desired effect when the matrix is implanted into the recipient. In another embodiment, the crystalline matrices contain a nucleic acid, for example, a vector containing a nucleotide sequence of interest, to facilitate gene therapy when the matrix is implanted into the recipient. It is contemplated that the choice of additives for a particular matrix will ultimately depend upon the intended function of the matrix.

The crystalline calcium sulfate matrix useful in the practice of the invention may be generated using a variety of starting materials. During the practice of the invention, exothermic calcium sulfate, for example, partially or fully dehydrated calcium sulfate, is combined with an aqueous solution. This results in an exothermic reaction, and the formation of new crystalline calcium sulfate.

Partially or completely dehydrated calcium sulfate useful in the practice of the invention can be manufactured by the calcination of calcium sulfate dihydrate ($CaSO_4.2H_2O$). Calcination can be controlled to produce partial or complete dehydration. Depending upon the method of calcination, different forms of the hemihydrate can be obtained. These forms are referred as α-hemihydrate or β-hemihydrate. The β-form is a fibrous aggregate of fine crystals with capillary pores, whereas the α-form consists of cleavage fragments and crystals in the form of rods or prisms. When the α-hemihydrate is mixed with water, the product obtained is stronger and harder than that resulting from β-hemihydrate.

Calcium sulfate hemihydrate is also known as plaster of paris, gypsum hemihydrate and, dried calcium sulfate. Calcium sulfate hemihydrate may be obtained from a variety of sources. For example, medical grade calcium sulfate hemihydrate is available commercially from U.S. Gypsum Company (Chicago, Ill.). Furthermore, the α-form of calcium sulfate hemihydrate can be obtained from LIFECORE Biomedical, Chaska, Minn., under the tradename CAPSET®.

Calcium sulfate matrices have been used for many years as supports for tissue formation. Moreover, calcium sulfate has been safely used in orthopedics for over 100 years and in dentistry for approximately 30 years (Peltier, *Am. J. Surg.* 97, 311, 1959; Calhoun et al. *J. Dent. Res.* 42, 1244, 1963; Sidqui et al. *Biomaterials* 16, 1327, 1995; Sottosanti, *Compend. Contin. Educ. Dent.* III, 226, 1992; Sottosanti *Pract. Periodontics Aesthetic. Dent.* 5, 61, 1993; Andreana, *J. Periodontal* 69, 601, 1998; Andreana, S., Covani, U. *Periodontal Insights* 5, 5, 1998; Sato et al. *Biomaterials* 19, 1895, 1998; Pecora et al. *Oral Surg. Oral Med. Oral Pathol. Oral Radiol. Endod.* 84, 424, 1997; Anson, D. *Compendium* 17, 895, 1996; Shaffer, C. D., App, G. R. *J. Periodontal* 42, 685, 1971; and Sottosanti, J. *Dent. Implantol. Update* 4, 69, 1993). These studies show no adverse effects of calcium sulfate such as an inflammatory reaction at the regeneration site.

The ability of calcium sulfate to support tissue formation (conductive activity) can be differentiated from the ability of a graft matrix to support tissue induction (inductive activity). An ideal regeneration matrix is tissuegenic, such that tissue formation is allowed (conductive activity) as well as encouraged (inductive activity).

One preferred calcium sulfate matrix comprises activated platelets, for example, calcium sulfate activated platelets, derived from platelet-rich plasma.

Platelet-rich plasma is plasma containing concentrated platelets, and can be developed from whole blood, more preferably, autologous whole blood, using a variety of techniques known in the art. For example, platelet-rich plasma useful in the practice of the invention can be prepared by subjecting whole blood to centrifugation to separate platelet-rich plasma from red blood cells. The platelet-rich plasma fraction then is subjected to a second round of centrifugation to produce a pellet of platelets and a supernatant of platelet-poor plasma. The majority of the platelet-poor plasma can be removed leaving the concentrated platelets and a small proportion of platelet-poor plasma behind. The platelet-poor plasma can then be used to re-suspend the concentrated platelets. Centrifuges useful in preparing platelet-rich plasma can be obtained from a variety of sources, including, for example, the PLA-CON™ centrifuge, which can be obtained from OCT USA Inc., Torrence, Calif.

Whole blood platelet counts, on average, range from $150 \times 10^3$ to $350 \times 10^3/\mu L$ of blood, however, in platelet-rich plasma a three or four fold increase in platelet concentration can be achieved. When activated, for example, by exposure to an agonist, platelets release the contents of dense bodies and α-granules, synthesize substances from membrane phospholipids, and initiate the coagulation cascade events (Hoffman et al. Hematology: Basic Principles and Practice. Philadelphia: *Churchill Livingstone Edition,* 2000). Platelet agonists typically are classified as strong or weak (Hoffman, et al., 2000, *supra*, and Blockmans et al. *Blood Reviews* 9, 143, 1995). By one definition, strong agonists are those that can trigger granule secretion even when aggregation is prevented. Thrombin and collagen are considered to be examples of strong agonists. By contrast, weak agonists, such as adenosine diphosphate (ADP) and epinephrine, require aggregation for secretion to occur. It has been reported that heat can act as a weak agonist in platelet activation (Kurabayashi et al. *Amer. J. Hematol.* 56, 244, 1997, and Gader et al. *Brit. J. Hematol.* 74, 86, 1990). Upon activation, the platelet dense bodies, the most rapidly secreted of platelet organelles, release ADP, as well as ATP and serotonin. The α-granules may release PDGF, TGF-β1, connective tissue activating peptide III (CATP III), thrombospondin, Factor V, fibrinogen, Factor XI, plasminogen activator inhibitor 1 (PAI-1), and adhesive proteins such as fibrinogen, fibronectin, von Willebrand Factor (vWF), and P-Selectin (also called GMP-140, structurally similar to E and L-selectins). Cytoplasmic factors that can be found in platelets are Factor XIII and platelet-derived endothelial cell growth factor (PDECGF).

Although calcium sulfate crystals serve to support bone growth, it has been found that the combination of the calcium sulfate with platelet-rich plasma provides the matrix with coagulation and repair factors that platelets usually provide in vivo. Many of these matrix elements and growth factors have been shown to be involved in the regulation of the proliferation and differentiation of cells and in tissue formation. It has been found herein that, when platelet-rich plasma is combined with calcium sulfate, the resulting exothermic reaction which can raise the temperature of the solution to between about 30° C. to about 50° C., and more preferably from about 40° C. to about 45° C., results in the formation of calcium sulfate crystals having activated platelets disposed thereon. This approach obviates the need for pre-activating the platelets in the platelet-rich plasma by exposure to thrombin or other agonists.

Another preferred calcium sulfate matrix comprises crystalline calcium sulfate and a growth factor. Preferred growth factors include, for example, BMP, FGF, PDGF, IGF and VEGF. PDGF elicits multifunctional actions with a variety of cells. PDGF is mitogenic to mesoderm-derived cells, such as fibroblasts, vascular smooth muscle cells, glial cells and chondrocytes. Also, PDGF is a potent chemoattractant and activator of neutrophils, monocytes and fibroblasts. Other actions of PDGF include its ability to regulate the synthesis and degradation of extracellular matrix proteins and to stimulate the synthesis of additional growth factors. Therefore, PDGF plays an essential role in the cellular response to tissue injury, both as a stimulant of mesodermal cell growth and activity, and as a chemoattractant to other cells involved in the repair process.

Matrices comprising crystalline calcium sulfate and a growth factor can be formed by combining exothermic calcium sulfate with the growth factor in an aqueous solution. The resulting exothermic reaction, which can raise the temperature of the solution to between about 30° C. to about 50° C., and more preferably from about 40° C. to about 45° C., results in the formation of calcium sulfate crystals containing the growth factor disposed thereon.

Another preferred calcium sulfate matrix comprises crystalline calcium sulfate and a nucleic acid. In a preferred embodiment, a nucleic acid vector encoding a gene of interest, for example, a gene encoding a tissue growth stimulating factor, is combined with the calcium sulfate matrix. Such matrices can be formed by combining exothermic calcium sulfate with a nucleic acid of interest in an aqueous solution. The resulting exothermic reaction, which can raise the temperature of the solution to between about 30° C. to about 50° C., and more preferably from about 40° C. to about 45° C., results in the formation of calcium sulfate crystals having the nucleic acid disposed thereon. The resulting matrices, when implanted, can be used to transfect cells at the implant site to facilitate gene therapy. While this embodiment is useful in stimulating bone growth, it can also be used to stimulate growth of other tissues, such as vascular or cardiovascular tissue.

Within the context of the present invention, the nucleic acid of interest can be a sense or antisense oligonucleotide, ribonucleic acid, deoxyribonucleic acid or a peptidyl-nucleic acid. These designations are conventionally used in molecular biology. Briefly, "sense" refers to a nucleic acid which possesses a sequence which is homologous with or identical to a target sequence, whereas antisense refers to a nucleic acid which possesses a sequence which is homologous with or identical to a sequence which is complementary to a target sequence. In conformity with the aims pursued by the present invention, the nucleic acid of interest contains at least one gene of interest and elements which enable it to be expressed in a cell or a host organism. The nucleic acid of interest is advantageously in the form of plasmid DNA or a viral vector (which vector is derived from an adenovirus, retrovirus, poxvirus, in particular from a vaccinia virus or an MVA virus, herpes virus, adenovirus-associated virus, etc.).

The choice of plasmids which can be used within the context of the present invention is vast. They can be of any origin whatsoever (prokaryotic or eukaryotic) or be formed by assembling various elements. In a general way, the plasmids are known to the skilled person. While a large number of them are available commercially, it is also possible to construct them using genetic manipulation techniques (Sambrook et al., 1989, Laboratory Manual, Cold Spring Harbor Laboratory Press, Cold Spring Harbor, N.Y.). The plasmid can be a cloning or expression vector which is derived, for example, from pBR322 (Gibco BRL), pUC (Gibco BRL), pBluescript (Stratagene), pREP4, or pCEP4 (Invitrogen). As an indication, the plasmid DNA, which is used in the present invention can be amplified and purified in accordance with the general practices of the art. Given that this is a technology which is now widely known, only a brief description will be given of the manner of proceeding, which consists of introducing the plasmid into producer cells (for example, *Escherichia coli*), culturing these cells under appropriate conditions (easily established by the skilled person on the basis of his general knowledge in this field and of the selection system carried by the plasmid) and recovering the plasmid DNA using the customary techniques (see, for example, Sambrook et al., 1989, supra). A purification step can also be envisaged, for example by carrying out the method described in French application FR96 11075, or any other method which is published in the literature.

The nucleic acid of interest can encode an antisense RNA and/or an mRNA which will then be translated into a polypeptide of therapeutic interest. The nucleic acid can be of the genomic, complementary DNA (cDNA) or mixed (minigene from which at least one intron has been deleted) type, and can be homologous or heterologous in relation to the host cell. The polypeptide which it encodes can correspond to all or part of a protein as is found in nature (native or truncated protein) or a mutant which exhibits improved and/or modified biological properties. The polypeptide can also be a chimeric polypeptide which is the result of fusing sequences of varied origin. The nucleic acid of interest can be obtained by chemical synthesis or by cloning (screening DNA libraries using suitable probes, PCR, etc.) and can be modified using the conventional techniques of molecular biology.

It can be advantageous, within the context of the present invention, to use a gene of interest which encodes promoter of tissue growth, for example, a growth factor, such as PDGF, or a BMP. It is noted that this list is not limiting and that other genes can also be employed.

The gene(s) which is/are carried by the nucleic acid of interest are placed under the control of the elements which are required for expressing them in the cell or host organism. These elements are elements which enable the genes to be transcribed into RNA and an mRNA to be translated into polypeptide.

Of these elements, the promoter is of particular importance. It can be isolated from any gene of eukaryotic or even viral origin and can be constitutive or regulatable. Alternatively, the promoter can be the natural promoter of the gene in question. Moreover, the promoter can be modified so as to improve its promoter activity, to suppress a region which inhibits transcription, to render a constitutive promoter regulatable or vice versa, to introduce a restriction site, etc. A variety of viral promoters, for example: the cytomegalovirus (CMV) promoter, the Rous sarcoma virus (RSV) promoter, the promoter of the HSV1 virus TK gene, the simian virus 40 (SV40) early promoter, and the adenoviral major late promoter (MLP) promoter, or of the eukaryotic promoters of the murine or human phosphoglycerate kinase (PGK), 1-antitrypsin (liver-specific), immunoglobulin (lymphocyte-specific), surfactant, CFTR (lung-specific) or actin (muscle-specific) genes, may be useful in the practice of the invention. Naturally, the nucleic acid of interest may in addition comprise elements which improve expression (intron sequence, signal sequence, nuclear localization sequence, transcription termination sequence, translation initiation site of the IRES or other type, etc.) or else the maintenance of the nucleic acid in the host cell (origin of replication, etc.). Such elements are known to the skilled person.

In another embodiment, the invention provides a multifunctional matrix comprising multiple components. For example, the multifunctional matrix may comprise an inner matrix or of core crystalline calcium sulfate and, optionally, a first growth factor, such as, VEGF. Disposed about the inner matrix or core can be an outer matrix comprising crystalline calcium sulfate and, optionally, a second, different growth factor, such as PDGF and/or TGF-β. This type of matrix may facilitate the formation of heterogeneous tissue that mimics the tissue to be replaced. In addition, one or more the inner matrix or the outer matrix may further comprise a nucleic acid, for example, the encoding a protein of interest for expression in the tissue.

In light of the foregoing general discussion, the specific examples presented below are illustrative only and are not intended to limit the scope of the invention. Other generic and specific configurations will be apparent to those persons skilled in the art.

EXAMPLE 1

This Example demonstrates that calcium sulfate may be used to activate platelets in platelet-rich plasma.

(a) Materials

In this Example, and in the following Examples, exothermic calcium sulfate was obtained from LIFECORE Biomedical, Chaska Minn., USA under the tradename CAPSET®, a medical grade calcium sulfate alpha-hemihydrate powder. Platelet-rich plasma was purchased from the American Red Cross, Buffalo N.Y. Bovine thrombin and Collagen Type I (from rat tail) were obtained from Sigma (Saint Louis, Mo.). Human recombinant Platelet-derived Growth Factor (rePDGF-BB) was obtained from Oncogene Research Products (Cambridge, Mass.). Anti-human Transforming Growth Factor-$\beta 1$ antibody (IgG fraction of antiserum, developed in Mouse) was obtained from Oncogene Research Products (Cambridge, Mass.). Anti-human Platelet-derived Growth Factor antibody (IgG fraction of antiserum, developed in Goat), Purified Mouse IgG and Purified Goat IgG were obtained from Sigma (Saint Louis, Mo.). Millicell®-PC, 0.4 µm culture plate inserts were purchased from Millipore Corp. (Bedford, Mass.). Extrude PS®, a polyvinylsiloxane impression material, was obtained from Kerr Corp. (Romulus, Mich.). Polyvinylsiloxane templates were sent to a Radiation Center for gamma-irradiation (Oregon State University, Corvallis Oreg.). $^3$H-thymidine (specific activity 1 mCi/ml) was obtained from ICN Radiochemicals (Irvine, Cailf.). Tissue culture media and supplements were purchased from GIBCO (Grand Island, N.Y.).

All other chemicals were of the highest grade available and purchased from various commercial sources.

(b) Methods

The following methods were used both in this Example and the subsequent Examples.

(i) Platelet-Rich Plasma Procurement

Platelet-rich plasma (Platelet Units) for research purposes was obtained from the American Red Cross. A Platelet Unit is a concentrate of platelets separated from a single unit of whole blood and suspended in a small amount of the original plasma. The usual Unit of Platelets contains no fewer than $1,100 \times 10^9$ platelets/L. To be consistent, the experiments were performed using units of the same and most common blood group (O Rh positive).

(ii) Human Osteoblastic Cell Isolation and Culture Conditions

Human primary osteoblast cultures were obtained from spongy human bone samples (Schmidt, R., Kulbe, K. D. *Bone Miner.* 20, 211, 1993; and Gotoh et al. *Bone Miner.* 8,239, 1990), which had to be removed and otherwise discarded during third molar extractions. All samples were collected from healthy young individuals (from 18 to 30 years old), after appropriate donor consent was obtained in accordance with the Institutional Human Subject Review Board. The bone samples were carefully cleaned off from soft tissue and eventually fragmented into suitable pieces (5 mm). After washes in Bone Cell Buffer (BCB), the pieces were placed in culture with BGJb media (Fitton-Jackson Modification) containing 10% Fetal Calf Serum (FCS) (Upstate Biotechnology, Lake Placid, N.Y.). Cells were allowed to seed out of the bone for 2-4 weeks until reaching 50% confluence in the flasks. The cells were maintained in a humidified, 5% $CO_2$ atmosphere incubator, at 37° C. Third to fifth passage cells were used in the following experiments.

These cells have shown to be enriched with alkaline phosphatase activity and osteocalcin level (Schmidt et al., 1993, supra; Beresford, J. N. et al. *Metab. Bone Dis. Rel. Res.* 5, 229, 1984; and Beresford, J. N. et al. *Endocrinology* 119, 1776, 1984).

(iii) Assay for Osteoblastic Cell Proliferation

Prior to the proliferation experiment, confluent flasks of human osteoblastic cells were briefly (2 minutes) trypsinized and scraped. The cells then were centrifuged and re-suspended in BGJb media (no FCS). The cell concentration was adjusted to $0.8 \times 10^5$ cells/ml. Following instructions by the manufacturer, an appropriate number of culture plate wells were prepared by adding 0.5 ml of BGJb media to each well, and Millicell®-PC 0.4 µm culture plate inserts were placed into wells and allowed to become properly moistened. Then, biomaterials were placed into sterile inserts for suspension cell culture. 0.5 ml of the cell suspension was added to each insert. The cells were allowed to attach and proliferate for 24 hours at 37° C.

To assess DNA synthesis, for the last four hours of the incubation time, 50 µL of $^3$H-thymidine solution (11 µCi/mL) was added to each insert. In this way, 1.0 µCi/mL final concentration per insert was reached. At the end of the time period, the media was gently removed by a Pasteur pipette and the samples washed three times with 0.5 ml of cold PBS in order to wash away all non-adherent cells. The inserts with the graft materials then were transferred into new plate wells. To assess the radioactivity associated with the cells, 0.5 ml of 1N NaOH/10 mM EDTA was previously added to each well and 0.5 ml of 1N NaOH/10 mM EDTA was then added into each insert. The samples were incubated at 37° C. for 1 hour. An aliquot (350 µL) of the insert supernatant and an aliquot (150 µL) of the well supernatant were collected and transferred to scintillation vials and neutralized with 0.5 ml of 1N HCl. Each sample received 10 ml of LIQUISC1NT™ scintillation fluid and was counted by liquid scintillation spectrometry. It is considered that the values for $^3$H-thymidine incorporation are reflective of both initial attachment of cells as well as the proliferation ability of cells.

(iv) Statistical Analysis of Data

Data were expressed as counts per minute (CPM) group. Each group included three samples. Differences among groups were statistically analyzed by ANOVA followed by Scheffe' multiple comparison test. A significance level of 0.1 was used ($\alpha=0.1$). Experiments were repeated three times.

(c) Experimental

One hour prior to the proliferation assays, aliquots of 750 mg of calcium sulfate were combined with a variety of different matrices as described in Table 1.

TABLE 1

| Group Name | Calcium Sulfate Combinations |
|---|---|
| CS | calcium sulfate and $H_2O$ |
| CS/ThrPRP | calcium sulfate and Thrombin activated PRP |
| CS/Thr50% PRP | calcium sulfate and 50% $H_2O$ + 50% Thrombin activated PRP |
| CS/PRP | calcium sulfate and non-activated PRP |
| CS/50% PRP | calcium sulfate and 50% $H_2O$ + 50% non-activated PRP |
| CS/Thr | calcium sulfate and $H_2O$ + Thrombin |
| CS/CollPRP | calcium sulfate and Collagen activated PRP |

TABLE 1-continued

| Group Name | Calcium Sulfate Combinations |
|---|---|
| CS/Coll | calcium sulfate and H$_2$O + Collagen |
| CS/PDGF-BB | calcium sulfate and PDGF-BB water solution (4 × 10$^{-9}$ M) |

The various matrices for testing were created as follows. Exothermic calcium sulfate in powder form was mixed with 279 μL of double-filtered distilled sterilized water (CS, control group) or with the same amount (279 μL) of thrombin pre-activated platelet-rich plasma (CS/ThrPRP) or non-pre-activated platelet-rich plasma RP (CS/PRP). Other test groups received half amount of double-filtered distilled sterilized water (139 μL) mixed with half amount (139 μL) of thrombin pre-activated platelet-rich plasma (CS/Thr50% PRP) or non-preactivated platelet-rich plasma (CS/50% PRP). Another test group received (279 μL) collagen activated platelet-rich plasma (CS/collPRP) or just (279 μL) collagen in water (CS/Coll).

Each group, created from the above amount of calcium sulfate, consisted of three identical samples. Using sterile polyvinylsiloxane templates, each of these samples was created as a standard size disk (4.5 mm in diameter and 2.5 mm in thickness). All samples were maintained at room temperature for the entire setting time (1 hour).

Activation of platelet-rich plasma was achieved in different ways. In the case of thrombin activation, according to Marx et al. (Marx et al. *Oral Surg. Oral Med. Oral. Pathol.* 85, 638, 1998), 1000 Units of bovine thrombin were mixed with 6 ml of platelet-rich plasma but with a single exception: CaCl$_2$ was not needed or used for dissolving thrombin. In case of collagen activation (Hoffman et al. Hematology: Basic Principles and Practice. Philadelphia: *Churchill Livingstone Edition*, 2000; Blockmans et al. *Thromb. Res.* 43, 445, 1986) (CS/CollPRP), 500 μg of collagen was dissolved in 279 μL of platelet-rich plasma. One more group (CS/PDGF-BB) was obtained by mixing calcium sulfate powder (750 mg) with 279 μL human rePDGF-BB water solution (4×10$^{31\ 9}$ M).

Scanning electron microscopy (SEM) evaluation of the combination of calcium sulfate and platelet-rich plasma (CS/PRP), and the combination of calcium sulfate and 50% platelet-rich plasma and 50% water (CS/50% PRP) showed structures integrated with the platelet-rich plasma organic matrix with no obvious difference with the overall organization of calcium sulfate alone. The calcium sulfate sample showed precipitation of the dihydrate crystals in the form of rods or prisms. Thus, upon combining the calcium sulfate with platelet-rich plasma, the characteristics and qualities of calcium sulfate microstructure were preserved and were also integrated with the platelet-rich plasma.

Figure 1:
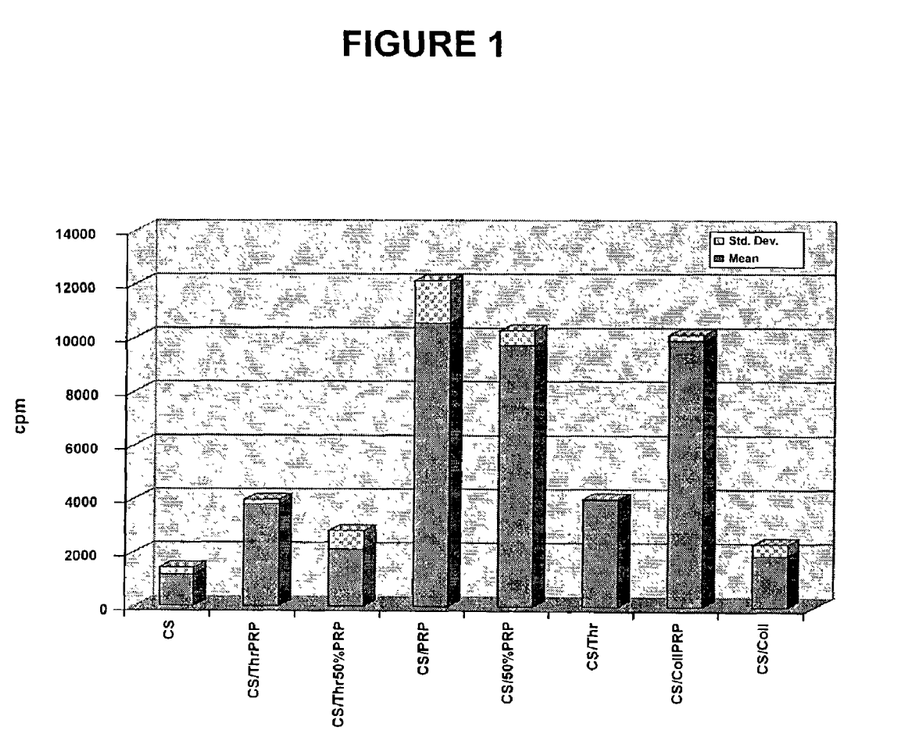
FIG. 1 is a bar chart showing the proliferation of primary human osteoblasts in the presence of different calcium sulfate matrix formulations.

The results of the osteoblastic cell proliferation assays are summarized in FIG. 1, wherein proliferation is indicated in counts per minute (cpm). The cells were cultured for 24 hours. $^3$H thymidine was added during the last two hours of incubation and the incorporation of $^3$H thymidine into DNA was taken as a measure of proliferation activity. Statistical analysis was performed by ANOVA followed by Scheffe' multiple comparison test (α=0.1; n=3).

Human primary osteoblastic cells cultured on CS/PRP samples, CS/50% PRP samples, and CS/CollPRP samples all exhibited the highest proliferation levels (p<0.001) with no statistically significant differences among these three groups. When platelet-rich plasma was pre-activated with thrombin (CS/ThrPRP or CS/Thr50% PRP), osteoblastic cells showed a lower level of proliferation compared to the non-activated or collagen-activated platelet-rich plasma samples (statistically significant difference, p<0.001). When calcium sulfate was mixed with thrombin alone (CS/Thr) or with Collagen alone (CS/Coll), a statistically significant difference was not appreciable in comparison to the control proliferation level (CS). These results demonstrate that it is possible to promote osteoblast proliferation by activating previously unactivated platelet-rich plasma with exothermic calcium sulfate. In fact, CS/PRP does not require thrombin activation to achieve the highest levels of osteoblastic proliferation and, therefore, the risks and limitations associated with the use of animal-derived protein (such as, for example, bovine spongiforme encephalopathy) are also avoided.

EXAMPLE 2

This example again demonstrates that platelet-rich plasma can be activated by exposure to calcium sulfate. Furthermore, this example demonstrates that part of the benefit of including platelet-rich plasma in the calcium sulfate matrices can be derived in part by the release of PDGF and/or TGF-β. Samples were created as summarized in Table 2 using the procedures essentially as described in Example 1, to generate the same disk sizes as in Example 1.

TABLE 2

| Group Name | Group Treatment (at 37° C.) |
|---|---|
| CS | PBS for 1 hour |
| CS/PRP | PBS for 1 hour |
| CS/PRP-Antibody or CS/Antibody | Anti-PDGF for 30 min then Anti-TGF-β1 for 30 min |
| CS/PRP-IgG | Goat IgG for 30 min then mouse IgG for 30 min |
| CS/PRP-Refrig | 6 hour incubation at 7-8° C. |
| CS/PDGF-BB | PBS for 1 hour |

In this example, the CS/PRP group was also refrigerator-treated (CS/PRP-Refrig), because calcium sulfate precipitation reaction is an exothermic reaction and achieves, during the 30-50 minutes setting time, a temperature of 40-45° C. (Phillips, 1991, supra, and O'Brien, 1989, supra). The refrigerator-treated samples were prepared following the usual preparation technique with the only difference that they were prepared 6 hours before and immediately incubated in refrigerator. In this way, during the entire setting time, samples were incubated at a constant temperature of 7-8° C., the exothermic reaction was slowed, and the material did not reach the usual setting temperature.

The following protocol was used in the antibody treatments: after preparation, samples were incubated in 1 ml of anti-PDGF solution (1.9×10$^{-7}$ M) for 30 minutes at 37° C., washed three times with 1 ml cold PBS, and then incubated in 1 ml of anti-TGF-β1 solution (1.7×10$^{-7}$ M) for 30 minutes at 37° C. (CS/PRP-Antibody and CS/Antibody). Control (CS/PRP-IgG) received the treatment with a solution of goat IgG (1.9×10$^{-7}$ M) followed by treatment with a solution of mouse IgG (1.7×10$^{-7}$ M). All other samples were maintained in 1 ml PBS for 1 hour at 37° C. Prior to the proliferation assay, all samples were washed three times with 1 ml cold PBS. The resulting matrices were assayed using the proliferation assay described in Example 1, and the resulting data analyzed as described in Example 1.

Figure 2:
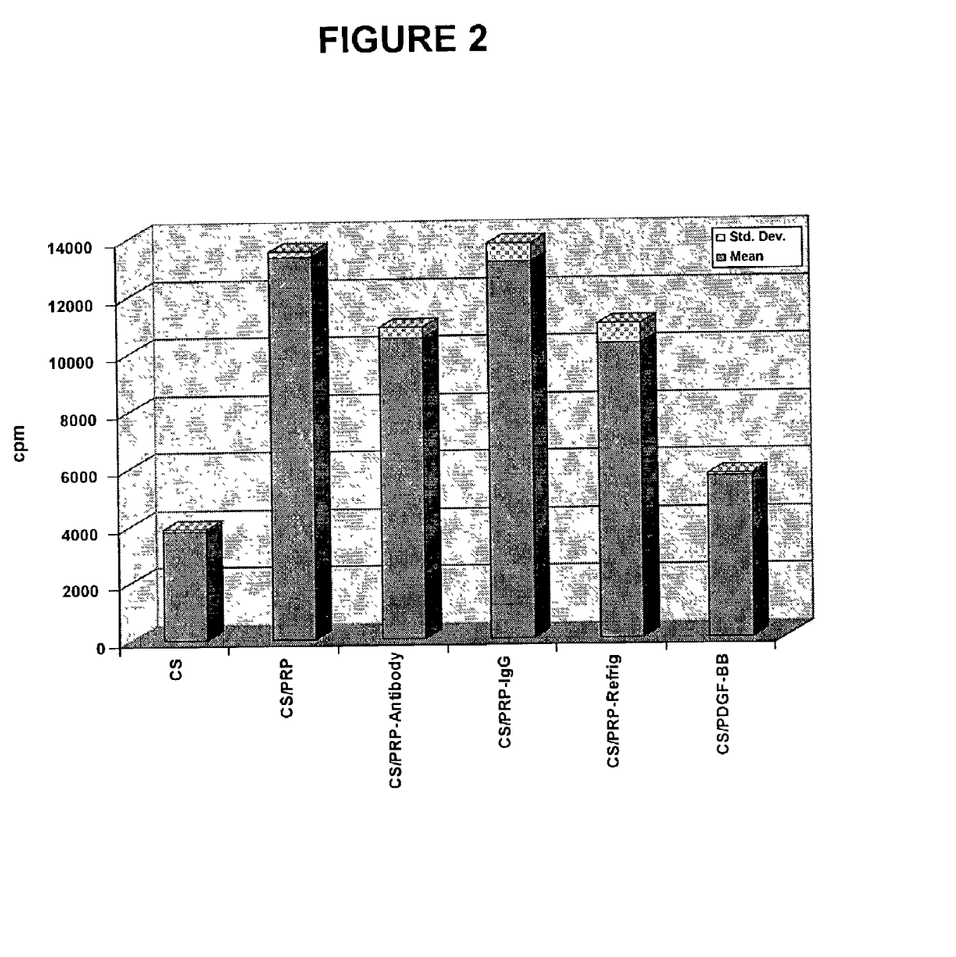
FIG. 2 is a bar chart showing the proliferation of primary human osteoblasts in the presence of different calcium sulfate matrix formulations.

The results are set forth in FIG. 2 wherein human primary osteoblastic cell proliferation is indicated in counts per minute (cpm). As shown in FIG. 2, human primary osteoblastic cells cultured on CS/PRP preparations or cultured on the same preparation after IgG-treatments (CS/PRP-IgG), exhibited the highest proliferation levels ($p<0.001$). Also, there is no statistically significant difference between these two groups. When the CS/PRP preparation was treated with an anti-human PDGF antibody and an anti-human TGF-β1 antibody (CS/PRP-Antibody), the proliferation level was lower than the previous two groups (statistically significant difference, $p<0.001$). CS/PRP-Refrig exhibited proliferation levels comparable to the specific antibody-treated group (CS/PRP-Antibody) and lower than CS/PRP or CS/PRP IgG-treated group (CS/PRP-IgG). Without wishing to be bound by theory, it appears that heat released during the exothermic crystalline precipitation reaction can serve at least in part to activate platelets. Also, when calcium sulfate was used as carrier for rePDGF-BB (CS/PDGF-BB) osteoblastic cells showed higher proliferation levels (statistically significant difference) compared to the control (CS).

Figure 3:
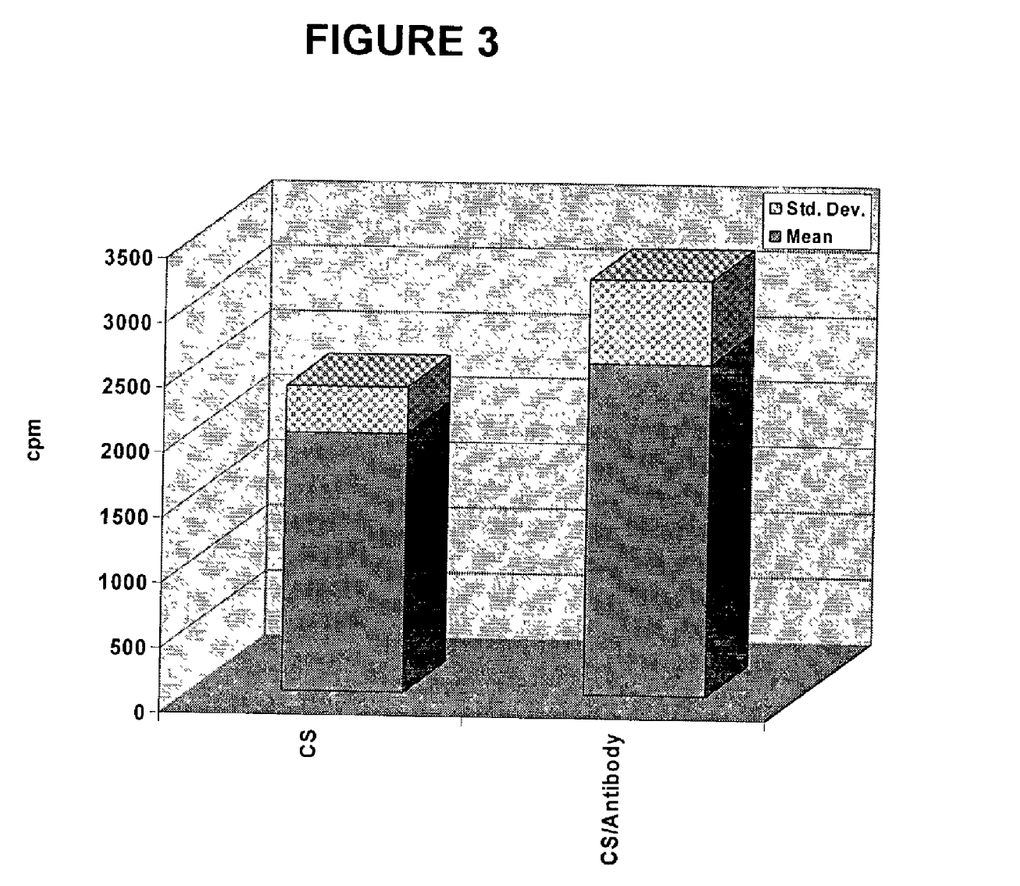
FIG. 3 is a bar chart showing the proliferation of primary human osteoblasts in calcium sulfate matrices that have or have not been pretreated with a combination of anti-PDGF and anti-TGF-β antibodies.

In a further control experiment, as shown in FIG. 3, no statistically significant difference was found between CS alone (CS) and CS previously treated with an anti-human PDGF antibody and an anti-human TGF-β1 antibody (CS/Antibody). The samples were prepared as described above, and the cell proliferation assay and the statistical analyses were performed as described in Example 1. Cells cultured on calcium sulfate alone (CS) or cultured on the same preparation after treatment with anti-human PDGF antibody and anti-human TGF-β1 antibody (CS/Antibody) exhibited comparable proliferation levels (no statistically significant difference). Inhibition of proliferation activity by antibody treatment was not noticeable. These specific antibodies per se do not inhibit proliferation and instead neutralized the activity of the platelet released PDGF and TGF-β1 in the CS/PRP samples.

EXAMPLE 3

This example provides comparative data, which indicates that calcium sulfate-platelet-rich plasma matrices can support a similar levels of osteoblastic cell proliferation as commercially available Grafton® Putty.

Samples were prepared in accordance with the teachings of Examples 1 and 2. Grafton® Putty, a demineralized bone matrix, was obtained from Osteotech Inc. (Eatontown, N.J.). The Grafton® Putty samples (GraftonPutty) were prepared using the same polyvinylsiloxane templates: the special malleability of this bone matrix compound permitted the preparation of samples of the same standard size disk as in all other preparations.

Figure 4:
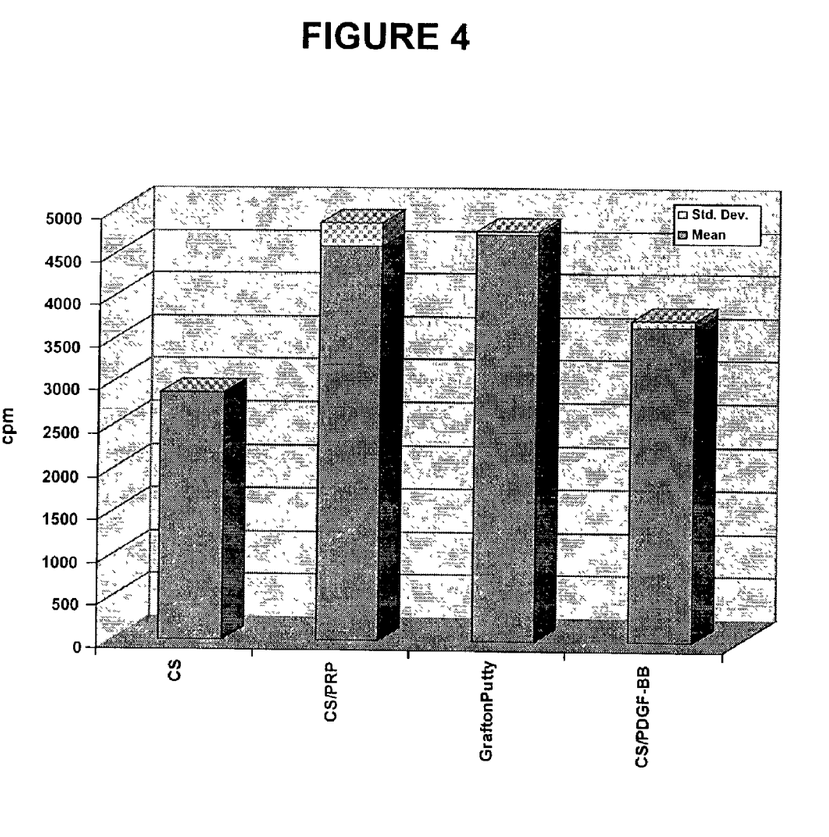
FIG. 4 is a bar chart showing the proliferation of primary osteoblasts in calcium sulfate matrices and Grafton® Putty.

The osteoblastic cell proliferation assay, and the data resulting therefrom was analyzed as discussed in Example 1. The results are summarized in FIG. 4. wherein human primary osteoblastic cell proliferation is indicated counts per minute (cpm). The results in FIG. 4 demonstrate that human primary osteoblastic cells cultured on CS/PRP samples exhibited proliferation levels comparable (no statistically significant difference) to Grafton® Putty, a demineralized bone matrix, and proliferation levels higher than CS or CS/PDGF-BB (statistically significant difference, $p<0.001$). Furthermore, when calcium sulfate was used as a carrier for rePDGF-BB (CS/PDGF-BB), osteoblastic cells showed higher proliferation levels (statistically significant difference, $p<0.001$) compared to calcium sulfate alone.

EXAMPLE 4

This example demonstrates the feasibility of using calcium sulfate based matrices in gene therapy protocols.

The following studies showed the capacity of calcium sulfate to be combined to naked DNA. Given the fact that calcium sulfate is physically able to carry and not alter the biological characteristics of the plasmid, delivery of the plasmid can be achieved over time by virtue of the slow resorption rate of calcium sulfate. When calcium sulfate powder was mixed to a water solution of plasmid DNA it could deliver a gene coding for Green Fluorescent Protein (pEGFP-Cl) into a human embryonic kidney cell line.

In the presence of HEPE buffered saline (HeBS) and $CaCl_2$, shattered particles of the combination of CS/plasmid were seeded onto human embryonic kidney cells (293 cells) at 75% confluency and transfection was evaluated at 24, 48 and 72 hrs FACScan flow cytometry (Becton Dickinson, San Jose, Calif.). At 72 hrs, the combination CS/plasmid containing 6 mg of calcium sulfate mixed with 5 µl of pEGFP-Cl water solution (20 µg of plasmid) was able to transfect almost 5% of the cell population. On the other hand, the traditional calcium phosphate precipitation (CPp) method was able to transfect 32.5% of the cell population when 10 µg of plasmid were seeded over the cell layer.

In another series of experiments, the ability of the supernatant of the shattered CS/plasmid suspended in $HeBS/CaCl_2$ to transfect cells was assessed. In this case, 30 µg of plasmid was incorporated into calcium sulfate. 293 cells were transfected with pEGFP-Cl. The cells were transfected using the calcium phosphate precipitation protocol or with the supernatant from CS/plasmid after suspension of CS/plasmid in $HeBS/CaCl_2$. After 72 hrs incubation, cells were harvested and analyzed by FACScan flow cytometry for fluorescence emission in the green (FL1) bandpass filter. Approximately 54% of the cells transfected with calcium phosphate were fluorescent, whereas approximately 10% of the cells transfected with the CS/plasmid supernatant were fluorescent. This experiment confirms that plasmids are released from the shattered CS/plasmid matrix and that, when released, they are still able to transfect cells. Accordingly, it appears that calcium sulfate does not alter the biological activity of plasmids and is able to deliver DNA into cells.

Incorporation by Reference

The disclosure of each of the patent documents, and scientific articles referred to herein is incorporated by reference herein.

Equivalents

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:
1. A bioactive matrix comprising:
a mixture of crystalline calcium sulfate and exothermic calcium sulfate activated platelets, wherein said mixture is obtained by contacting an exothermic calcium sulfate salt with a platelet-containing fluid, wherein the platelets are not preactivated prior to contact with the exothermic calcium sulfate salt, wherein said platelets are obtained from an autologous source and wherein the bioactive matrix is substantially free of thrombin activity.

2. The matrix of claim 1, further comprising a growth factor.

3. The matrix of claim 2, wherein the growth factor is platelet-derived growth factor.

4. The matrix of claim 1, further comprising a nucleic acid.

5. The matrix of claim 4, wherein the nucleic acid comprises a preselected gene expressible at a locus.

6. The matrix of claim 1, wherein the bioactive matrix is dimensioned to permit the infiltration, proliferation and differentiation of cells at a preselected locus.

7. The matrix of claim 6, wherein the cells are bone progenitor cells.

8. The matrix of claim 6, wherein the cells are osteoblast cells.

9. The matrix of claim 2, further comprising a nucleic acid.

10. The matrix of claim 1, wherein the platelets are activated by calcium sulfate hemihydrate.

11. The matrix of claim 10, wherein the calcium sulfate hemihydrate is α-hemihydrate.

12. The matrix of claim 10, wherein the calcium sulfate hemihydrate is β-hemihydrate.

13. A method of promoting bone formation at a preselected locus in a mammal, comprising:
   providing to the locus the bioactive matrix of claim 1, wherein the bioactive matrix promotes bone formation at the locus.

14. The method of claim 13, wherein the locus is a bone defect.

15. The method of claim 14, wherein the bone defect is a cavity or a fracture.

16. The method of claim 15, wherein the fracture is a non-union fracture.

17. The method of claim 13, wherein the bioactive matrix further comprises a growth factor.

18. The method of claim 17, wherein the growth factor is platelet-derived growth factor.

19. The method of claim 13, wherein the bioactive matrix further comprises a nucleic acid.

20. The method of claim 19, wherein the nucleic acid comprises a preselected gene expressible at the locus.

21. The method of claim 20, wherein the nucleic acid is capable of being transfected into and expressed by a cell at the preselected locus.

22. The method of claim 13, wherein the bioactive matrix is dimensioned to permit the infiltration, proliferation and differentiation of cells at the preselected locus.

23. The method of claim 22, wherein the cells are bone progenitor cells.

24. The method of claim 22, wherein the cells are osteoblast cells.

25. The method of claim 13, wherein the activated platelets are disposed within platelet-rich plasma.

26. The method of claim 13, further comprising the step of manipulating the bioactive matrix to produce a shape of interest at the preselected locus.

27. A method of expressing a nucleic acid of interest at a bone defect, the method comprising:
   introducing the matrix of claim 5 at the bone defect and permitting expression of the nucleic acid at the bone defect.

28. The method of claim 27, wherein said nucleic acid encodes a growth factor.

29. The method of claim 28, wherein said growth factor comprises an osteogenic growth factor.

30. The method of claim 27, wherein said nucleic acid encodes a protein selected from the group consisting of platelet-derived growth factor and a bone morphogenic protein.

31. The method of claim 30, wherein said nucleic acid further comprises a promoter sequence.

32. The method of claim 27, wherein the bone defect is a cavity or a fracture.

* * * * *